United States Patent [19]

Reul et al.

[11] 4,218,783

[45] Aug. 26, 1980

[54] PROSTHETIC CLOSURE ELEMENT FOR THE REPLACEMENT OF THE MITRAL AND TRICUSPID VALVE IN THE HUMAN HEART

[75] Inventors: Helmut Reul, Düren, Fed. Rep. of Germany; Dhanjoo N. Ghista, Sunnyvale, Calif.

[73] Assignee: Dr. E. Fresenius, Chem.-Pharm. Industrie KG, Bad Homburg, Fed. Rep. of Germany

[21] Appl. No.: 944,379

[22] Filed: Sep. 21, 1978

[30] Foreign Application Priority Data

Sep. 22, 1977 [DE] Fed. Rep. of Germany ....... 2742681

[51] Int. Cl.² .............................................. A61F 1/22
[52] U.S. Cl. ........................................ 3/1.5; 137/521; 137/855
[58] Field of Search ..................... 3/1.5; 137/855, 517, 137/521

[56] References Cited

U.S. PATENT DOCUMENTS

| | | | |
|---|---|---|---|
| 15,192 | 6/1856 | Peale | 3/1.5 X |
| 2,682,057 | 6/1954 | Lord | 3/1.5 |
| 3,548,417 | 12/1970 | Kischer | 3/1.5 |
| 3,589,392 | 6/1971 | Meyer | 3/1.5 X |
| 3,898,701 | 8/1975 | LaRussa | 3/1.5 |
| 3,926,215 | 12/1975 | MacLeod | 3/1.5 X |
| 4,011,601 | 3/1977 | Clune et al. | 3/1.5 |

FOREIGN PATENT DOCUMENTS 1443221 7/1976 United Kingdom .......................... 3/1.5

OTHER PUBLICATIONS

Mitral Valve Prosthesis (Dr. Bruce Paton) The Bulletin of The Dow Corning Center for Aid to Medical Research, Midland, Mich., vol. 5, No. 4, p. 16, Oct. 1963.

*Primary Examiner*—Ronald L. Frinks
*Attorney, Agent, or Firm*—Andrus, Sceales, Starke & Sawall

[57] ABSTRACT

A prosthetic heart valve has a tubular valve housing, a suture ring, and a membrane-like gate supported within the housing. The flexible membrane is generally elliptical in shape and is fastened in the housing along half its periphery. Flexure of the membrane moves it between an open position which permits blood flow through the housing and a closed position which blocks the flow path of the housing.

13 Claims, 17 Drawing Figures

PROSTHETIC CLOSURE ELEMENT FOR THE REPLACEMENT OF THE MITRAL AND TRICUSPID VALVE IN THE HUMAN HEART

BACKGROUND OF THE INVENTION

1. Field of the Invention

The present invention relates to a prosthetic closure element for the replacement of the mitral and tricuspid valve in the human heart having a valve housing, a suture ring for the attachment of the valve housing in the tissue and a flap or gate supported within the housing.

2. Description of the Prior Art

It is known in the replacement of the mitral valve to employ ball or disc valves. The results obtained with such closure elements are, however, not satisfactory. The complications resulting therefrom can be traced back mainly to three reasons: mechanical reasons, biological reasons, and material reasons or a combination of these three. The mechanical reasons for valve defects are material fatigue, breaking, or deformation of the valve body, either under the influence of mechanical loading or through chemical corrosion. Under failures of a biological nature, inflammation and rejection of the materials foreign to the body frequently occur. Mechanics of flow resulting conditions, as for example, distruction of red corpucles in zones of high localized shearing stresses and thrombi formation in zones of low flow velocities are a further important reason. Shearing stresses and velocity distributions with the above noted characteristics are found with all valve body gates which hinder the blood stream in different ways:

(a) through the valve body itself, which forces the blood to flow through an annular clearance between the valve body and the gate ring (with ball and disc valves) or in two separate flow channels with differing flow losses (with pivoted disc flaps);

(b) through the valve body support (cages, pivots) and (c) through the gate ring which is comprised of the gate seat and suture ring.

In contrast to the properties of existing artificial mitral valves, the natural valves permit a central, undisturbed flow control with soft opening and closing action and without backflow. An additional great disadvantage of most artificial valves is the psychic strain on the patient through the opening and closing noise.

It will be appreciated that the presently used types of mitral valves do not correspond to the functional requirements. These requirements, which arise out of the anatomical and flow mechanics criteria of the left ventricle, are not taken into consideration by the presently existing constructions. It is, as a matter of fact, to be emphasized that the valves used today are employed with only minor modifications of the suture ring for the aortic as well as the mitral positions, even though fully different demands are presented for these positions.

The reasons of defect of the heart valves can be summarized as follows:

(a) diastolic pressure gradients, which cause intensified pressure work, flow losses, and insufficient filling of the ventricle.

(b) high local shearing stresses, which cause harm or destruction to cellular blood constituents;

(c) return flow with the valve closed in an order of magnitude of 5% to 10%; and (d) thrombi formation in zones of low flow velocity.

SUMMARY OF THE PRESENT INVENTION

The present invention takes as its object, to provide, in particular, a closure element suitable for the replacement of the mitral or tricuspid valve in the human heart, with which the foregoing noted disadvantages are overcome and, in particular, achieves a soft, undisturbed flow control, both in the open as well as in the closed position, and avoids thrombi producing stagnations as well as blood injuring, high shearing stresses.

These objects are obtained through the initially described closure element which is characterized in that the flap is formed in the form of a thin flexible membrane and represents generally that part of the surface of an elliptical cylinder $$\frac{y^2}{R_i^2} + \frac{z^2}{(R_i \tan \alpha)^2} = 1$$

which is cut out by a circular cylinder $x^2 + y^2 = R_i^2$, whereby $R_i$ is the radius of the circular cylinder and $\alpha$ is half the valve opening angle and whereby the angle between the central axes of the two cylinders in the closed condition of the membrane amounts to 90° and in the open condition amounts to 90° − 2° $\alpha$. The valve housing represents generally a part of the surface of a circular tube with an inner radius $R_i$ and an outer radius $R_a$, which is cut by the elliptical cylinder under an angle of 90°. The membrane is fastened along half the periphery of the cut edge between a pair of extreme points of the housing.

In contrast to the known ball or disc valves the solution of the present invention concerns itself with a membrane valve and, indeed, with a single membrane mitral valve which, under consideration of the physiological and engineering criteria would resemble the natural mitral valve and accompanying flow dynamics which are asserted through the anatomy of the human heart.

From anatomy it is known that the inclination of the mitral valve plane relative to the longitudinal axis of the aorta amounts, on the average, to 45°. The base of the aorta, in turn, has, on the average, an inclination of 20° relative to the vertical middle axis of the left ventricle and consequently a similar inclination angle with respect to the chamber wall. The valve plane lies in an angle of 65° to the vertical heart axis. From flow dynamics of the natural mitral valve it can be postulated that the blood should flow in without turbulence or deflection through the valve in the ventricle. In other words, the inflow should result approximately parallel to the main axis of the ventricle and therewith to the chamber wall. In order to insure undisturbed inward flow, the membrane must thusly be controlled also to lie parallel to the chamber wall. From this consideration an ideal opening angle of 65° results for the membrane.

During the expulsion phase (systole) the mitral valve should put up a minimal flow resistance to the blood streaming out of the ventricle: is should, rather, conduct the flowing blood in the direction of the discharge vessel. For this purpose, the valve membrane should, in the closed condition, lie parallel to the mitral valve plane.

The mitral valve closure rests on the force which is produced from the annular eddy in the ventricle, and on the delay of the blood stream through the mitral valve opening at the end of the flowing in phase (diastole). When the ventricle is to be filled, the mitral valve opens very fast. The blood stream entering the chamber strikes the chamber point, spreads sideward and upward behind the pair of sails in a natural mitral valve and simultaneously produces a strong ring-like eddy in the hollow ventricle, which holds the pair of sails in a stable position. When the inward flow slows down, the pressure difference on two sides of the sails causes a movement in the direction of the closed position. Therethrough is the mitral valve readily closed, before the chamber contraction and, therewith, the pumping phase begins.

This functional relationship leads to the conclusion that only a membrane valve whose membrane has somewhat the same form, flexibility and spatial position as the large sail of the natural mitral valve is in the position to take advantage of these physiologically asserted flow dynamics phenomena. This aspect is taken into consideration with the construction according to the invention. It has been shown that the eddy produced behind the membrane effects a chamber closure before the beginning of the chamber contraction.

With the solution according to the invention, anatomical, physiological, and biomechanical criteria are collectively taken into consideration. In particular, the construction guarantees a soft, undisturbed flow control both in the open as well as in the closed position and thereby avoids thrombi producing stagnations and high shearing stresses harmful to the blood. Also, the closure element according to the invention permits a central flow control without an obstruction in the blood stream, simulating the physiological flow within the ventricle, uses the accompanying flow forces in the closing operation, reduces or eliminates, therethrough, the backflow, and works without any peculiar sound.

It is emphasized that the closure element formed in accordance with the invention is the first development of a valve for the mitral or tricuspid position having the construction parameters so defined that it fulfills the specific anatomical and flow mechanics criteria deduced from the normal physiology.

The closure element according to the invention fulfills the following requirements:

(a) undisturbed flow in the open condition where the membrane lies parallel to the ventricle walls;

(b) minimal flow resistance and diversion of the blood to the outflowing vessel in the closed condition in which the membrane is fully seated in the valve housing and lies parallel to the valve plane;

(c) low shearing stresses based on the large opening surfaces and avoidance of flow obstructions in the blood stream;

(d) no stagnation regions as no flow obstuctions exist; and (e) production and use of the chamber eddy in assisting the valve closing. Thus, a minimization of backflow and an optimization of the functional efficiency is produced.

A further great advantage of the closure element according to the invention lies in the avoidance of disturbing working sounds which, with conventional valves, are produced through the striking of the closing element on the metal valve ring and the metal cage. The soft landing of the flexible membrane of the closure element according to the invention produces no noise. The opening and closing times are, as contrasted to conventional valves, reduced, the inertia of the thin membrane (0.2–0.4 mm) being very small in comparison to ball or flap closing elements. These circumstances guarantee that the membrane can react, almost delay free on the quickly changing pressure gradients within the ventricle and thereby more closely approach the natural valve than any other existing heart valve.

The closure element formed in accordance with the invention has three main components: the membrane, the valve housing and the suture ring which is necessary to fasten the closure element in the tissue. The membrane moves, in the operation of the closure element, back and forth between a closed end position and an open end position whereby, with the transition from the closed to the open position it invertingly changes or reverses its bend. It represents generally that part of the surface of an elliptical cylinder $$\frac{y^2}{R_i^2} + \frac{z^2}{(R_i \tan \alpha)^2} = 1$$

which is cut out by a circular cylinder $x^2 + y^2 = R_i^2$, whereby $R_i$ is the radius of the circular cylinder and $\alpha$ is half the valve opening angle. In the closed condition of the membrane the angle between the central axes of the two cylinders amounts to 90° and in the open position to $90° - 2° \alpha$. The valve housing in which the membrane is supported represents generally a part of the exposed surface of a circular tube with an inner radius $R_i$ and an outer radius $R_a$, which is cut by the elliptical cylinder under an angle of 90°. The major axis of the ellipse of this elliptical cylinder is equal to the inner radius of the valve housing ($R_i$). In order to insure that the membrane is seated, in the closed condition of the closure element, fully in the housing and therewith to make the projection of the membrane surface parallel to the plane of the closure element, the minor axis of the ellipse is equal to the height of the valve housing (exclusive of a rim with the height s necessary for the fastening of the suture ring) and therewith equal to $R_i \tan \alpha$. The outer radius $R_a$ of the valve housing is so selected that the membrane with a preferred embodiment of the closure element rests against the housing wall in the closed condition and on this is supported. With this preferred embodiment, the surface of the membrane is, in its closed position, bordered through two planes running parallel to the y-axis which respectively under an angle $\alpha$ and $\beta$ are oppositely inclined to the x-axis, whereby the angle $\beta$ equals arc tan $(R_i/R_a \tan \alpha)$. In other words, with this embodiment the membrane in the x-axis direction is formed slightly longer than $2R_i$, so that in the closed condition, it extends in the x-axis direction from the housing inner edge to the oppositely lying housing outer edge. In this manner a leak-proof closing of the membrane is insured.

In the open condition, the membrane lies somewhat parallel to the ventricle axis. This means that the central axes of the two cylinders must intersect at an angle of $90° - 2° \alpha$. Suitably, the angle $\alpha$ amounts to 20°–45°, whereby an embodiment with an angle of 32.5° is preferred.

The closure element according to the invention functions in the following manner. In the diastole, when the atrium pressure exceeds the ventricle pressure, the membrane opens wide. The blood then enters parallel to the ventricle wall and fully undisturbed in the ventricle through the closure body and forms an eddy behind the membrane sail. In the systole, when the ventricle pressure exceeds the atrium pressure the membrane closes rapidly and is thereby fully seated in the housing. There thus results an undisturbed flow parallel to the membrane and therewith to the mitral valve plane.

Preferably, the membrane is fastened on the housing inner side by means of an affixing ring extending about the half periphery of the housing. The rest of the free edge of the membrane is supported in the closed condition preferably on the housing wall. A suitable recess is appropriately arranged on the housing inner side over the half periphery of the housing for the accommodation of the affixing ring.

As already mentioned the minor axis of the ellipse of the membrane generating cylinder part corresponds to the valve housing height, except for a housing edge, which is required for the fastening of the suture ring. The valve housing possesses thus altogether a height of $R_i \tan \alpha + s$, where s is the dimension of the surrounding housing rim and typically amounts to $(0.1-0.3) 2R_i$. In order to fasten the suture ring on the valve housing the surrounding housing rim is provided in a particular embodiment with a peripheral recess on its outer side.

Naturally, a succession of variations relative to the form of the membrane and the valve housing occur. For example, the membrane can be formed with strengthening ribs, which in the closed condition of the membrane extend parallel to the x-axis. These strengthening ribs are preferably arranged on the side of the membrane away from the valve housing, in order to render possible a smooth contact of the membrane on the valve housing wall. It is clear that through the arrangement of such ribs, the flexibility of the membrane is reduced; the ribs should thus be provided only to such an extent that the functional quality of the membrane is not therethrough impaired.

With another altered embodiment, the valve housing has at least one support parallel to the x-axis extending transverse to the opening. This support serves as additional abutment for the membrane which in the closed position is supported on the strut. Through this arrangement the flow properties of the closure element are naturally disadvantageously influenced. These disadvantageous properties are therefore to be reconciled with the advantages obtained through the improved support of the membrane.

A further altered embodiment is distinguished in that the outer side of the valve housing is tapered in the direction of its extreme points. The extreme points of the valve housing and the portions of the affixing ring occurring at these locations can, however, also in the peripheral direction be rounded off. Finally, there exists the possibility that the areas about the extreme points of the valve housing are elastically formed for the absorption of impacts

BRIEF DESCRIPTION OF THE DRAWING

In the following, a preferred embodiment of the closure element according to the invention is described with the aid of the accompanying drawings.

FIG. 2 is a perspective view of one embodiment of the closure element of the present invention showing it in the open condition in FIG. 2a and in the closed condition in FIG. 2b.

FIG. 3 shows the closure element of FIG. 2 in the xz-plane (FIG. 3a), yz-plane (FIG. 3b), and xy-plane (FIG. 3c) in the closed condition.

FIG. 4 shows the closure element of FIG. 2 in the xz-plane (FIG. 4a), yz-plane (FIG. 4b), and xy-plane (FIG. 4c) in the open condition.

FIGS. 5a, b, and c are orthographic projection views of the closure element shown in FIG. 2 in the xz-, yz-, and xy-planes with FIG. 5a showing an oblique projection of the flat membrane.

FIG. 6a shows the valve housing in section and FIG. 6b shows the valve housing in a view from beneath and FIG. 6c is a section along the line A-A in FIG. 6b.

DETAILED DESCRIPTION OF THE PREFERRED EMBODIMENT

Figure 1:
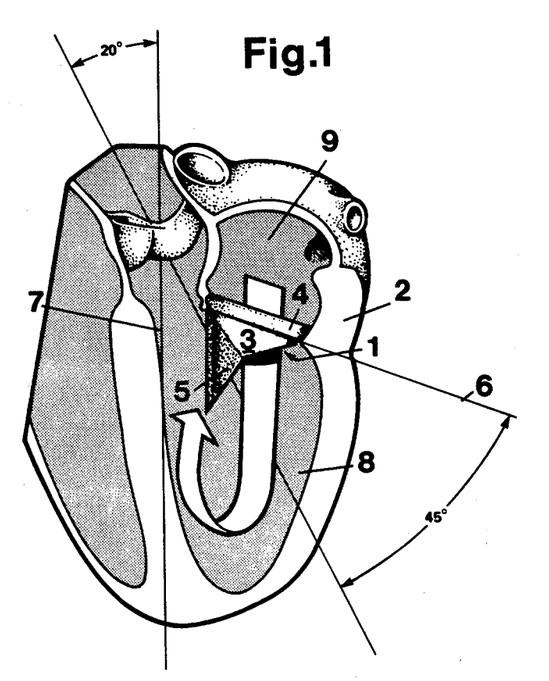
FIG. 1 is a partially cut-away view showing the spatial location of the closure element according to the invention in the human heart.

Turning now to FIG. 1, there is shown a closure element 1 constructed in accordance with the invention, which is inserted in place of the natural mitral valve in a human heart 2. The mitral valve plane is identified in FIG. 1 with the numeral 6. The closure element 1 is shown in the open condition and is formed of a valve housing 3, a suture ring 4, which serves to fasten the valve housing in the tissue, and a membrane 5 movable back and forth between an open position and a closed position. In the open condition the membrane takes a position approaching parallelism to the vertical middle axis of the left ventricle 7 and therewith also, in general, to the wall of the chamber 8. The inclination of the mitral valve plane 6 relative to the longitudinal axis of the base of the aorta amounts on the average to 45°. The base of the aorta, in turn, has, on the average, an inclination of 20° relative to the vertical middle axis of the left ventricle and therewith also the the chamber wall. Thus, the angle between the valve plane 6 and the vertical heart axis 7 amounts to 65°.

The closure element according to the invention is shown in a position in FIG. 1 by which, as a result of the atrium 9 pressure exceeding the pressure in the ventricle, the membrane has been widely opened and blood flows in the ventricle 8 parallel to the chamber walls. This blood forms an eddy behind the membrane sail. In the systole, when the ventricle pressure exceeds the atrium pressure, the membrane is rapidly transferred to the closed position which is exemplarily shown in FIG. 2b. The membrane is in this position fully seated in housing 3. There thus results an undisturbed flow parallel to the membrane and therewith to the mitral valve plane 6.

Figure 2A:
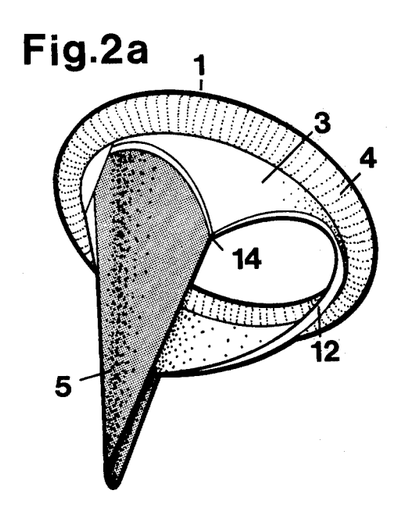
Figure 2B:
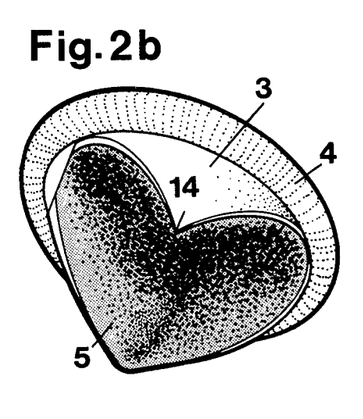
Figure 3A:
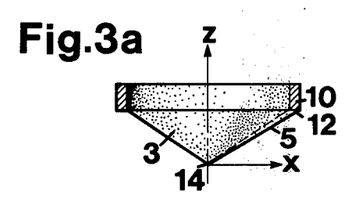
Figure 3B:
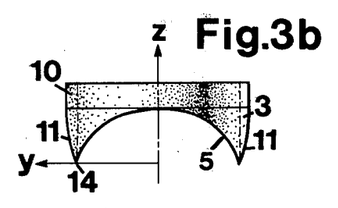
Figure 3C:
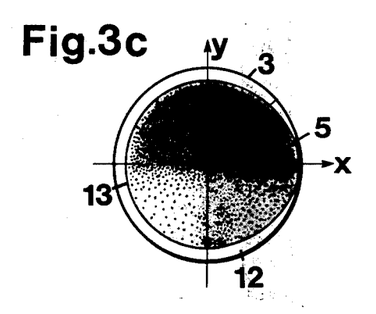
Figure 4A:
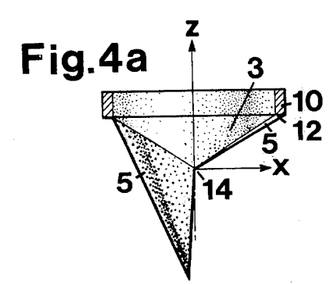
Figure 4B:
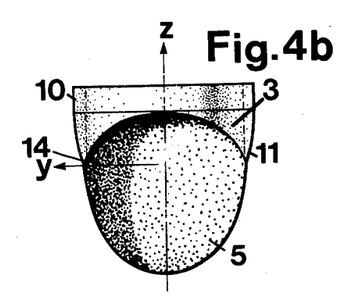
Figure 4C:
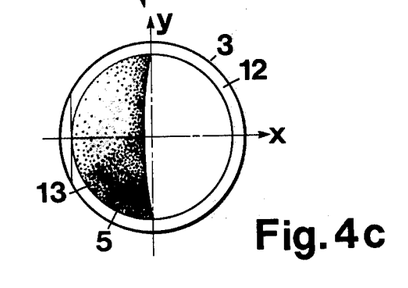

In FIGS. 2-4 the closure element according to the invention is shown both in the open, as well as in the closed, position in perspective view and in the xz-, yz-, and xy-planes. It will be appreciated that the gate is formed in the form of a thin flexible membrane 5. This membrane generally represents that part of the surface of an elliptical cylinder $$\frac{y^2}{R_i^2} + \frac{z^2}{(R_i \tan \alpha)^2} = 1$$

which is cut out by a circular cylinder $x^2 + y^2 = R_i^2$, whereby $R_i$ is the radius of the circular cylinder and $\alpha$ is half the valve opening angle and whereby the angle between the central axes of the two cylinders in the closed condition of the membrane amounts to 90° and in the open condition 90° $-2\alpha$. As will be seen from FIG. 1 almost ideal operation is obtained when the valve opening angle $2\alpha$ amounts to 65°, that is, the membrane, in this case, lies, in the open condition, substantially parallel to the ventricle wall. When the angle $\alpha$ lies in a range of 20°–45° can also, however, good results be obtained. The valve housing 3 represents generally a part of the surface of a circular tube with an inner radius $R_i$ and an outer radius $R_a$ which is cut by the elliptical cylinder under an angle of 90°. The membrane 5 is fastened along the half periphery of the line of intersection 13 between this pair of cylinders between the pair of extreme points 14 of the line of intersection.

With the herein exemplarily disclosed embodiment, the membrane is not entirely symmetrical; particularly in the x-direction it is formed slightly longer than $2R_i$, so that in the closed condition, it extends in the x-direction from the housing inner edge to the oppositely lying housing outer edge. The membrane can thus support itself in this manner in the closed condition on the edge 12 of the housing wall. That means that the surface of the membrane in its closed condition is bordered through two edges running parallel to the y-axis which, respectively, under an angle $\alpha$ and $\beta$ are oppositely inclined to the x-axis, whereby the angle $\beta$ equals arc tan $(R_i/R_a \tan \alpha)$. The angle $\beta$, which is inserted in FIG. 5, is thus slightly smaller than angle $\alpha$.

As can be particularly appreciated from FIGS. 3 and 4, the chamber housing does not fully correspond to the form of a circular tube. Rather, the outside of the valve housing 3 is formed tapered in the direction of its extreme points 14. These tapered regions 11 are not of essential significance for the functioning of the closure element according to the invention. The height of the valve housing corresponds to the minor axis of the ellipse of the membrane generating cylinder part plus the surrounding rim 10, which serves essentially for the mounting of suture ring 4. The height s of this surrounding rim 10 amounts to approximately (0.1–0.3) $2R_i$.

Figures 5A, 5B, 5C:
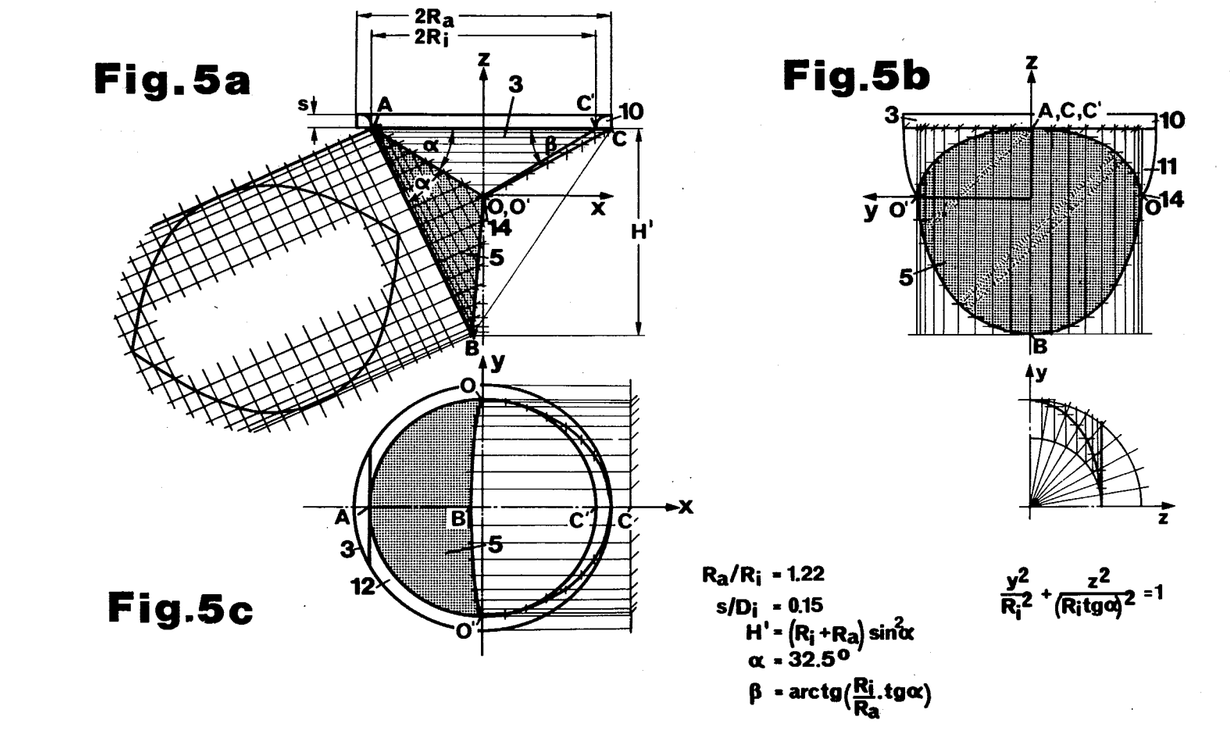

In FIG. 5, the membrane and the valve housing are shown in projection view in the perspective planes, whereby additionally, the development of the membrane and the construction of the ellipse are shown.

Figure 6A:
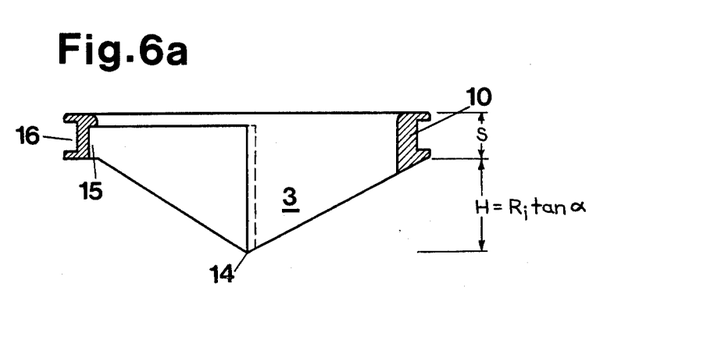
FIGS 6a, b and c are views of the valve housing shown in FIG. 2, whereby
Figure 6B:
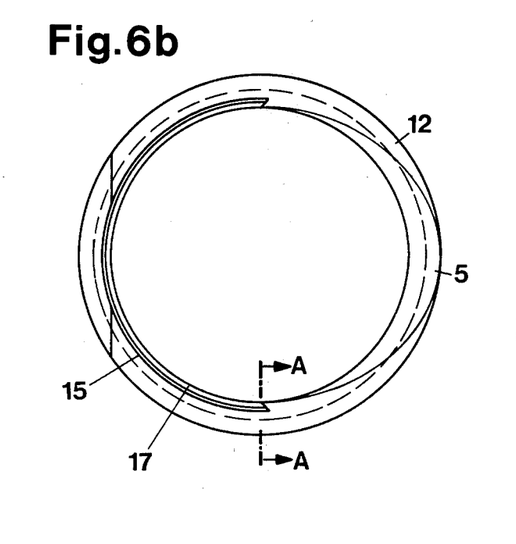
Figure 6C:
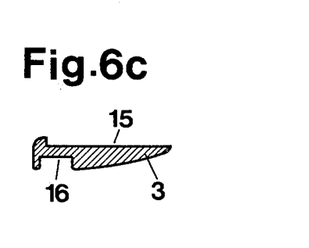

Referring now to FIG. 6, it will be appreciated that FIG. 6a is a representation of the valve housing 3 in section. FIG. 6b shows a view of the valve housing from below. The peripheral rim 10 of the valve housing 3 has on its inner side a recess 15 suitable for the accommodation of affixing ring 17 for the membrane. This recess extends on the inside of the housing over half the periphery of the housing between the pair of extreme points 14 and is variable in dimension as shown in FIG. 6a and 6c. The membrane is fastened in this recess by means of an affixing ring, which, for example, can be provided by means of a thin-walled plastic or metal ring with the aid of a shrink fit. Naturally, other fastening techniques for these affixing rings will also occur, for example, with the aid of screws. It is of significance that the affixing ring occurs entirely in the recess 15 so that a smooth housing inner surface emerges which presents no resistance to blood passing through. On the outer side of housing periphery 10 is likewise a recess 16 arranged which serves for the accommodation of the suture ring which is required for the fastening of the valve housing in the tissue. FIG. 6b shows clearly how the membrane 5 is fastened in a peripheral half of the valve housing and supports itself on the other half against the rim 12 of the housing wall, so that it extends from the intersection point of the housing wall with the x-axis to the outer edge of the housing wall.

The outer radius $R_a$ of the valve housing (3) is (1.1–1.3) times the inner radius $R_i$.

As concerns the production of the individual parts of the closure element according to the present invention, it should be noted, that the membrane for example, can be produced by a dipping process. Thus, a preformed master pattern is dipped in a fluid solution of a plastic compatible with the blood, for example, a block copolymer based on a polyurethane or silicone rubber. The number of dipping operations determines the membrane thickness which should amount to approximately 0.2–0.4 mm. The valve housing 10 can be produced from a metal compatible with the blood, for example, titanium alloy or stainless steel. Alternatively, the use of pyrolytic carbon or a plastic compatible with the blood would be possible. The suture ring is preferably produced out of knit or woven fabric.

Figure 7:
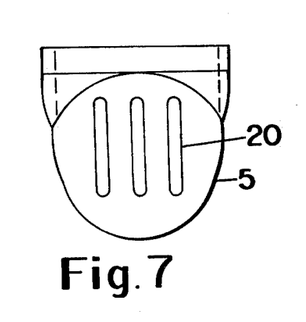
FIG. 7 is a view of another embodiment of the present invention having strengthening ribs on the membrane.
Figure 8:
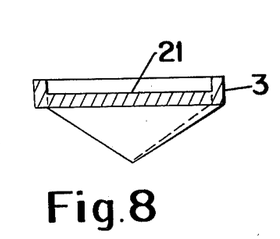
FIG. 8 is a view of another embodiment of the present invention having a support extending transverse to the opening of the valve housing.

FIG. 7 shows a closure element 1 in which membrane 5 has strengthening ribs 20. FIG. 8 shows a valve housing 3 having support 21 parallel to the X-axis extending transverse to the opening. Support 21 serves as additional abutment for membrane 5 in the closed position.

We claim:

1. A prosthetic closure element for the replacement of the mitral and tricuspid valve in the human heart having a valve housing, a suture ring for the attachment of the valve housing in the tissue and a flap movably mounted within the housing, characterized in that the flap is formed in the form of a thin flexible membrane and generally represents that part of the surface of an elliptical cylinder $$\frac{y^2}{R_i^2} + \frac{z^2}{(R_i \tan \alpha)^2} = 1$$

which is cut out by a circular cylinder $x^2 + y^2 = R_i^2$, whereby $R_i$ is the radius of the circular cylinder and $\alpha$ is half the valve opening angle and whereby the angle between the central axes of the two cylinders in the closed condition of the membrane amounts to 90° and in the open condition amounts to 90° $-2\alpha$; that the valve housing (3) represents generally a part of the surface of a circular tube with an inner radius $R_i$ and an outer radius $R_a$ which is cut by the elliptical cylinder under an angle of 90°; and that the membrane (5) is fastened along the half periphery of the intersection edge (13) between the pair of extreme points (14) of said valve housing.

2. The closure element according to claim 1 characterized in that the surface of the membrane (5) in its closed condition is bordered through two planes running parallel to the y-axis, which, respectfully, under an angle of $\alpha$ and $\beta$ are oppsingly inclined to the x-axis, whereby the angle $\beta$ equals arc tan $(R_i/R_a \tan \alpha)$.

3. The closure element according to claim 1 characterized in that the outer radius $R_a$ of the valve housing (3) is (1.1–1.3) $R_i$.

4. The closure element according to claim 1, characterized in that the angle $\alpha$ lies in a range of 20°–45°.

5. The closure element according to claim 1, characterized in that the membrane (5) is fastened on the inner side of the housing by means of a affixing ring (17) extending around half the housing periphery.

6. The closure element according to claim 5 characterized in that on the housing inner side a recess suitable for the accommodation of the affixing ring (17) is arranged.

7. The closure element according to claim 1 characterized in that the valve housing (3) has a height of $R_i \tan \alpha + s$, whereby s is the height of a peripheral housing rim (10) of said valve housing and amounts to approximately (0.1–0.3) $2R_i$.

8. The closure element according to claim 7 characterized in that the housing rim (10) is provided, on its outer side, with a peripheral recess (16) for accommodating the suture ring.

9. The closure element according to claim 1 characterized in that the membrane (5) is provided with strengthening ribs which extend parallel to the x-axis in the closed condition of the membrane.

10. The closure element according to claim 1 characterized in that the valve housing (3) has at least one support extending parallel to the x-axis transverse to the opening.

11. The closure element according to claim 1 characterized in that the outer side of the valve housing (3) is tapered in the direction of its extreme points (14).

12. The closure element according to claim 5 characterized in that the extreme points (14) of the valve housing (3) and the areas of the affixing ring positioned on these points are rounded off in the peripheral direction.

13. The closure element according to claim 1 characterized in that the regions about the extreme points (14) of the valve housing (3) are elastically formed for the absorption of impacts.

* * * * *

UNITED STATES PATENT AND TRADEMARK OFFICE
CERTIFICATE OF CORRECTION

PATENT NO. : 4,218,783
DATED : August 26, 1980
INVENTOR(S) : Helmut Reul et al

It is certified that error appears in the above-identified patent and that said Letters Patent are hereby corrected as shown below:

Column 2, Line 29, Cancel "$90°-2°\alpha$" and substitute therefor---$90°-2\alpha$---

Column 2, Line 62, Cancel "is" and substitute therefor ---it---

Column 4, Line 27, Cancel "$90°-2°\alpha$" and substitute therefor---$90°-2\alpha$---

Column 4, Line 49, Cancel "(Ri/Ra tan $\alpha$)" and substitute therefor---$(\frac{Ri}{Ra} \tan \alpha)$---

Column 4, Line 59, Cancel "$90°-2°\alpha$" and substitute therefor---$90°-2\alpha$---

Column 7, Line 35, Cancel "(Ri/Ra tan $\alpha$)" and substitute therefor---$(\frac{Ri}{Ra} \tan \alpha)$---

UNITED STATES PATENT AND TRADEMARK OFFICE
CERTIFICATE OF CORRECTION

PATENT NO. : 4,218,783
DATED : August 26, 1980
INVENTOR(S) : Helmut Reul et al

It is certified that error appears in the above-identified patent and that said Letters Patent are hereby corrected as shown below:

Column 8, Line 68, (Claim 2)  Cancel "(Ri/Ra tan $\alpha$)" and substitute therefor --- $(\frac{Ri}{Ra} \tan \alpha)$ ---

Signed and Sealed this

*Thirteenth* Day of *January 1981*

[SEAL]

*Attest:*

SIDNEY A. DIAMOND

*Attesting Officer*     *Commissioner of Patents and Trademarks*